(12) United States Patent
DeCarlo

(10) Patent No.: US 6,592,540 B2
(45) Date of Patent: Jul. 15, 2003

(54) TAMPON APPLICATOR WITH LUBRICATED TIP

(76) Inventor: Tracy DeCarlo, 55 Shaler Ave., Fairview, NJ (US) 07022

( * ) Notice: Subject to any disclaimer, the term of this patent is extended or adjusted under 35 U.S.C. 154(b) by 64 days.

(21) Appl. No.: 09/681,713

(22) Filed: May 29, 2001

(65) Prior Publication Data

US 2002/0128590 A1 Sep. 12, 2002

Related U.S. Application Data

(60) Provisional application No. 60/274,578, filed on Mar. 12, 2001.

(51) Int. Cl.[7] ................................................ A61F 13/20
(52) U.S. Cl. .................................................... 604/12
(58) Field of Search ........................... 604/11–18, 904, 604/385.18

(56) References Cited

U.S. PATENT DOCUMENTS

| | | | | |
|---|---|---|---|---|
| 3,139,886 A | * | 7/1964 | Tallman et al. | |
| 3,791,385 A | * | 2/1974 | Davis et al. | |
| 3,884,233 A | * | 5/1975 | Summey | |
| 4,312,348 A | * | 1/1982 | Friese | |
| 4,421,504 A | * | 12/1983 | Kline | |
| 4,690,671 A | * | 9/1987 | Coleman et al. | |
| 5,676,647 A | * | 10/1997 | Cimber | |
| 2002/0026140 A1 | * | 2/2002 | McNamara | |

* cited by examiner

Primary Examiner—Dennis Ruhl
(74) Attorney, Agent, or Firm—Richard A. Joel, Esq.

(57) ABSTRACT

A tampon applicator comprises inner and outer hollow members with a tampon mounted within the outer member. The inner member is telescopically mounted within the hollow outer member with one end surface adapted to contact the tampon and its other end surface extending outwardly to act as a plunger. A lubricant is located within the outer member secured therein by inner and outer seals. The tampon with a lubricating coating is ejected with the application of force to the slideable plunger.

2 Claims, 1 Drawing Sheet

TAMPON APPLICATOR WITH LUBRICATED TIP

CROSS REFERENCE TO RELATED APPLICATIONS

This application is related to Provisional Application Serial No. 60/274,578 filed Mar. 12, 2001.

BACKGROUND OF INVENTION

1. Field of the Invention

This invention relates to tampons and in particular to tampon applicators having a tip with lubricant to facilitate the placement of a tampon into a body cavity.

2. Description of Related Art Including Information Disclosed under 37 CFR 1.97–1.98

Catamenial tampons are inserted into a woman's vagina to absorb menstrual fluid, blood and other body secretions. One conventional way of inserting such tampons is with the use of an applicator.

The traditional two-piece applicator design includes a hollow applicator having a tampon telescopically mounted therein and a plunger element which forces the tampon outwardly. Considerable effort has been directed to reduce the force required to expel the tampon but the problem of ease and comfort during the insertion still exists. The direct insertion of the dry absorbent fibers of a tampon often causes irritation of the vaginal walls. Plastic applicators can pinch or cut tissue during insertion and paper applicators require an increased expulsion force which can cause the applicator to deform or the tampon to be inserted incorrectly.

Among the relevant prior art patents are U.S. Pat. Nos. 4,690,671 to Coleman and 5,569,177 to Fox, et al.

The Coleman U.S. Pat. No. 4,690,671 discloses an inserter equipped with a moveable and removable fluid reservoir at the place of tampon exit and conduits which carry a portion of the fluid to the other end of the tampon. The tampon inserter is unduly complicated, expensive and requires a considerable force to rupture the fluid seal.

Fox, et al U.S. Pat. No. 5,569,177 features an insertion tip which extends outwardly from an inner telescopically mounted member and within which a tampon is mounted. The tampon is expelled through the tip when force is applied to the tampon. Various tips are disclosed in the patent.

Also of interest is U.S. Pat. No. 3,335,726 which discloses a lubricating tampon having a container triangular in cross-section having a gathered inner edge around an opening through which a tear-string extends and with a lower surface scored on circles to release a lubricant on pulling the string. The V-shaped plastic container stretches as the tampon is ejected.

The present invention is distinctly different from the prior art and has the unique advantages of being inexpensive, easy to use, and comfortable in use.

SUMMARY OF THE INVENTION

This invention relates to tampons and more particularly to tampon applicators which are easy to use and comfortable in use.

In the invention, the tampon applicator includes inner and outer hollow members with a tampon mounted within the outer member. The inner member is telescopically mounted within the hollow outer member with its end surface adapted to contact the tampon. The inner member projects outwardly from one end of the outer member and is slideable therewithin to serve as a plunger. A lubricant is mounted within the other end of the outer member which is of suitable material such as plastic or coated paper or paperboard or any other material that could be used in connection with an applicator.

In use, an outer seal is removed or broken from the outer member so that the lubricant is exposed. The movement of the inner member forces the tampon outwardly through a fragile inner seal with the lubricant spreading along the tip and sides of the tampon. The use of the lubricant permits easy and comfortable insertion of the tampon lessening the chances of irritating sensitive tissues.

Accordingly, an object of this invention is to provide a new and improved tampon applicator which is easy to use.

Another object of this invention is to provide a new and improved tampon applicator which is inexpensive and provides lubrication for ease of insertion.

A more specific object of this invention is to provide a new and improved tampon applicator which includes a tampon and a telescopic plunger mounted within an outer cylinder and a lubricant reservoir at the tip of the cylinder which may be sealed within the cylinder by a removable strip or other material, the plunger forcing the tampon outwardly with a coating of lubricant when force is applied to the plunger.

BRIEF DESCRIPTION OF DRAWINGS

The above and other objects and advantages of this invention may be more clearly seen when viewed in conjunction with the accompanying drawings wherein.

DETAILED DESCRIPTION

Figure 1:
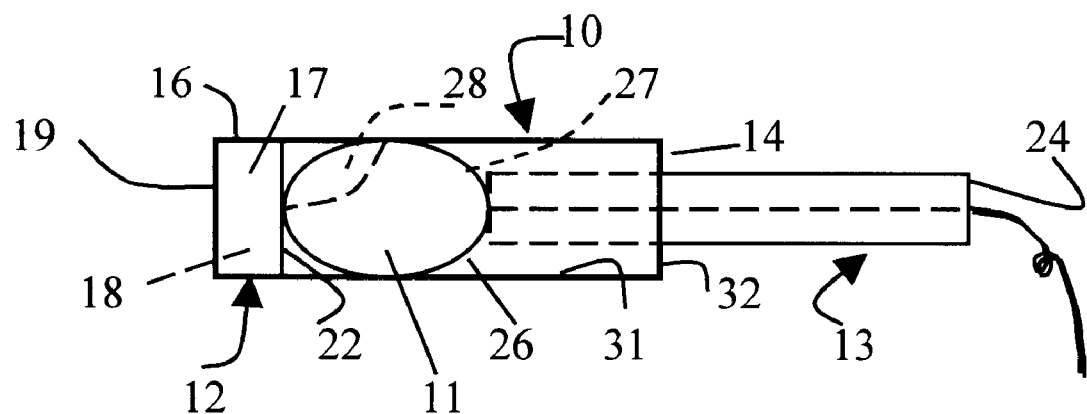
FIG. 1 is a cut-away front view of the invention with portions shown in phantom.
Figure 2:
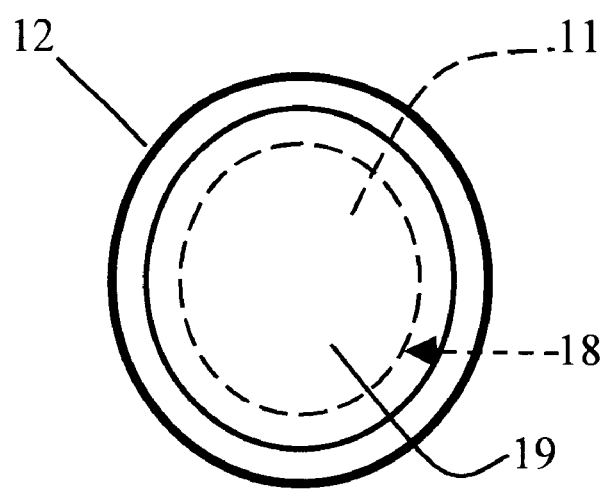
FIG. 2 is an end view of the invention.

Referring now to the drawings, the invention comprises a unique tampon applicator 10. the tampon 11 is shown in phantom mounted within the hollow cylinder 12. A second cylinder 13 is telescopically mounted within the end 14. The cylinder 13 acts as a plunger in engagement with the tampon 11 which is preferably of cotton or other natural materials. The withdrawal string which is connected to the tampon 11 extends outwardly from the cylinder 13.

A lubricant reservoir 17 is located at the other end 16 of cylinder 12. The lubricant 18 is maintained within the cylinder 12 by a peelable seal 19 which extends across the open end 21. A second seal 22 and a surface 31 of appropriate material such as plastic or latex maintains the lubricant 18 within the cylinder 12 without the danger of seepage. With a tear-off seal 19, it is possible to have a stronger seal. There are no strings at the end 16 which could accidentally be pulled on shipping, storage or use. Further, there is no need to have a perforated internal structure connected to a string which would increase the cost.

The lubricant may be various creams or petroleum jelly or other materials soluble with additives to assure the sterility thereof. The exterior surface of cylinder 13 can also be lubricated or contain an additive if desired. Suitable lubricants and additives include any of the pharmaceutically accepted lubricants or additives conventionally used in tampon applicators. Such lubricants and additives include organic compounds, long change aliphatic groups, such as derivatives of fatty acids, for example stearamides and oleamides.

The hollow cylinder 12 may be a material such as plastic material or paper coated with a polyethylene or polypropylene film to contain the lubricant. The internal coated surface is impervious to the lubricant preventing leakage. The second cylinder is of a sufficiently rigid material that it can exert the necessary force to push the tampon through the lubricant into the vagina.

An external coating of wax or polyethylene may be applied to the exterior of the second cylinder 13 to facilitate sliding movement within the outer cylinder 12 or the cylinder 13 may be spaced from the internal walls 31 of the outer cylinder 12 and extend through an aperture 32 in end 24.

In an alternate embodiment, the seal 19 is merely ruptured by the outward movement of cylinder 13 and there is no need to tear off the protective surface 19. The second seal 22 is normally ruptured by the movement of the cylindrical plunger 13. In this embodiment, the seal 19 may not be as strong as in the tear-off embodiment since deformation of the tampon 11 or misdirection thereof may result.

In use, the cylinders 12 and 13 are grasped and pressure is applied to the end 24 of cylinder 13. The end 26 drives the tampon 11 outwardly within cylinder 12 breaking the internal lubricant seal 22 and driving the tampon 11 outwardly from the end 21. The tampon 11 passes through the lubricant 18 wherein a thin coating adheres to the outer surface 27 and forward portion 28 to facilitate insertion into the vagina. The problem caused by dry fibers and excessive force is thus averted.

While the invention has been explained by a detailed description of certain specific embodiments, it is understood that various modifications and substitutions can be made in any of them within the scope of the appended claims, which are intended also to include equivalents of such embodiments.

A tampon applicator includes inner and outer hollow members with a tampon mounted within the outer member. The inner member is telescopically mounted within the hollow outer member with one end surface adapted to contact the tampon and its other end surface extending outwardly to act as a plunger. A lubricant is located within the outer member secured therein by inner and outer seals. The tampon with a lubricating coating is ejected with the application of force to the slideable plunger.

What is claimed is:

1. A tampon applicator for insertion of tampons comprises:

a first hollow cylinder having a front open end portion and a rear open end portion; a tampon located within said cylinder;

a second hollow cylinder slidably mounted within the first cylinder and having a first end portion engaging the tampon within the first cylinder and a second end portion extending outwardly from the rear end portion of the first cylinder, said second cylinder having an exterior coated with a material to facilitate movement within the first cylinder;

a reservoir having a lubricant mounted therein comprising the front open end portion of the first cylinder, said cylinder having a first seal extending across the front open end portion and a second seal extending across said cylinder at a spaced distance from the first seal, wherein pressure is applied to the second end portion of the second cylinder causing said cylinder to move within the first cylinder driving the tampon through the lubricant and outwardly from the first cylinder for insertion thereof.

2. A tampon applicator for insertion of tampons comprises:

first hollow cylinder having a front open end portion and a rear open end portion;

a tampon located within said cylinder;

a second hallow cylinder slidlably mounted within the first cylinder and having a first end portion engaging the tampon within the first cylinder and a second end portion extending outwardly from the rear end portion of the first cylinder;

a reservoir having a lubricant mounted therein comprising the front open end portion of the first cylinder, said cylinder having a first seal extending across the front open end portion and a second seal extending across said cylinder at a spaced distance from the first seal, wherein the first cylinder further includes an interior wall surrounding the reservoir, said wall including a coated material impervious to the lubricant and wherein;

pressure is applied to the second end portion of the second cylinder causing said cylinder to move within the first cylinder driving the tampon through the lubricant and outwardly from the first cylinder for insertion thereof.

* * * * *